United States Patent [19]
Shen

[11] Patent Number: 6,010,688
[45] Date of Patent: Jan. 4, 2000

[54] POLYHYDRIC ALCOHOL STABILIZED ANTIPERSPIRANT SALT SOLUTIONS

[75] Inventor: Yan-Fei Shen, Canton, Mass.

[73] Assignee: The Gillette Company, Boston, Mass.

[21] Appl. No.: 08/881,237

[22] Filed: Jun. 25, 1997

[51] Int. Cl.[7] .................................................. A61K 7/34
[52] U.S. Cl. .............................................. 424/66; 424/68
[58] Field of Search ................................. 424/65, 66, 68

[56] References Cited

U.S. PATENT DOCUMENTS

| | | | |
|---|---|---|---|
| 3,405,153 | 10/1968 | Jones et al. | 260/429 |
| 3,420,932 | 1/1969 | Jones et al. | 424/47 |
| 3,523,130 | 8/1970 | Jones et al. | 260/448 |
| 3,947,556 | 3/1976 | Jones et al. | 423/463 |
| 4,359,456 | 11/1982 | Gosling et al. | 424/68 |
| 4,775,528 | 10/1988 | Callaghan et al. | 424/66 |
| 4,781,917 | 11/1988 | Luebbe et al. | 424/65 |
| 4,818,512 | 4/1989 | Markavian et al. | 423/462 |
| 4,859,446 | 8/1989 | Abrutyn et al. | 423/462 |
| 4,871,525 | 10/1989 | Giovanniello et al. | 423/463 |
| 4,900,534 | 2/1990 | Inward | 423/463 |
| 4,944,933 | 7/1990 | Inward | 423/462 |
| 5,202,115 | 4/1993 | Vincenti et al. | 424/66 |
| 5,225,187 | 7/1993 | Carmody | 424/66 |
| 5,234,677 | 8/1993 | Murray et al. | 423/462 |
| 5,296,623 | 3/1994 | Katsoulis et al. | 556/27 |
| 5,330,751 | 7/1994 | Curtin et al. | 424/66 |
| 5,356,609 | 10/1994 | Giovanniello et al. | 423/462 |
| 5,463,098 | 10/1995 | Giovanniello et al. | 556/27 |
| 5,486,347 | 1/1996 | Callaghan et al. | 423/623 |
| 5,643,558 | 7/1997 | Provancal et al. | 424/66 |

FOREIGN PATENT DOCUMENTS

| | | |
|---|---|---|
| 7191 | 1/1980 | European Pat. Off. . |
| 295070 | 12/1988 | European Pat. Off. . |
| 404533 | 12/1990 | European Pat. Off. . |
| 405598 | 1/1991 | European Pat. Off. . |
| 52-99994 | 8/1977 | Japan . |
| 5-58867 | 3/1993 | Japan . |
| 2048229 | 12/1980 | United Kingdom . |
| 2113666 | 8/1983 | United Kingdom . |

*Primary Examiner*—Shelley A. Dodson
*Assistant Examiner*—Michael A. Williamson
*Attorney, Agent, or Firm*—Stephan P. Williams

[57] ABSTRACT

The present invention relates to methods of making enhanced efficacy antiperspirant salts and particularly stabilized aqueous polyhydric alcohol solutions of such salts. One such method involves stabilizing an aqueous solution of an enhanced efficacy antiperspirant salt by adding an effective amount of a polyhydric alcohol having from 3 to 6 carbon atoms and from 3 to 6 hydroxyl groups. A second disclosed method involves preparing an enhanced efficacy aluminum antiperspirant salt by heating an aqueous solution of an aluminum antiperspirant salt in the presence of a polyhydric alcohol having from 3 to 6 carbon atoms and from 3 to 6 hydroxyl groups at a temperature of at least 50° C. for a time sufficient to convert the salt to an enhanced salt. A third disclosed method is an improvement in the method of making an aluminum hydroxy halide or an aluminum hydroxy nitrate by reacting aluminum with an aqueous solution of aluminum halide or aluminum nitrate (or with aqueous hydrogen halide or nitric acid), wherein the improvement comprises including a polyhydric alcohol having from 3 to 6 carbon atoms and from 3 to 6 hydroxyl groups in the reaction mixture. Also disclosed are compositions produced by the foregoing methods.

27 Claims, No Drawings

POLYHYDRIC ALCOHOL STABILIZED ANTIPERSPIRANT SALT SOLUTIONS

BACKGROUND OF THE INVENTION

The present invention relates to methods of making enhanced efficacy antiperspirant salts and particularly stabilized solutions of such salts.

Enhanced efficacy aluminum and aluminum-zirconium antiperspirant salts are well known and are described, for example, in GB 2,048,229, EP 405,598, U.S. Pat. No. 4,359,456, U.S. Pat. No. 4,775,528, U.S. Pat No. 4,859,446, U.S. Pat. No. 4,871,525, U.S. Pat. No. 4,900,534, U.S. Pat. No. 4,944,933, U.S. Pat. No. 5,202,115, U.S. Pat. No. 5,234,677, U.S. Pat. No. 5,296,623, U.S. Pat. No. 5,330,751 and U.S. Pat. No. 5,356,609. These enhanced salts are also known to rapidly revert back to their non-enhanced state (for example, as evidenced by an HPLC peak 4 to peak 3 area ratio of 0.3 or less) in aqueous solution, particularly at concentrations greater than 20%. Consequently, the enhanced antiperspirant salts are generally only available in powder form.

A preferred method of preparing enhanced efficacy antiperspirant salts comprises heating a 5 to 18% aqueous solution of aluminum salt, preferably aluminum chlorohydrate, at a sufficient temperature and for a sufficient time to provide an HPLC peak 4 to peak 3 area ratio of at least 0.5, preferably at least 0.7, and most preferably at least 0.9, with at least 70% of the aluminum contained in said peaks. The aqueous solution may be obtained by diluting a standard commercially available 50% salt solution with water to the desired concentration, which is preferably 8 to 15%. The temperature and time of heating may be adjusted as necessary to achieve the desired degree of conversion to the enhanced state. Generally, longer times are required at lower temperatures. It is preferred to heat above 50° C., more preferably at 70° to 100° C., for at least two hours, more preferably for at least 10 hours or more. Excellent results are obtained by heating at about 80° to 85° C. for about 15 to 20 hours.

An alternative method of preparing aqueous solutions of enhanced efficacy aluminum hydroxy halides is that described in U.S. Pat. No. 4,859,446 and U.S. Pat. No. 5,356,609, the disclosures of which are incorporated herein by reference. In this method aluminum metal is reacted with aluminum halide, typically aluminum chloride, or with hydrogen halide, typically hydrochloric acid, in water at a temperature of about 50° to 100° C., the concentration of the reactants being such as to provide an aqueous solution of aluminum hydroxy halide, typically aluminum chlorohydrate, of about 5 to 25%, preferably about 8 to about 15%, by weight.

A number of references describe various ways of making alcohol soluble antiperspirant actives. These references include, for example, U.S. Pat. No. 3,405,153, U.S. Pat. No. 3,420,932, U.S. Pat. No. 3,523,130, and U.S. Pat. No. 3,947,556. In each case concentrated solutions of the antiperspirant active (i.e., in the 40 to 50% range) are employed as a starting material and the product is obtained as a powder, which must then be redissolved in the desired alcohol solution. Such techniques pre-date the availability of enhanced efficacy salts and are not believed to be applicable thereto as they would likely cause reversion to the non-enhanced state. In EP 7191 there is exemplified a process for making a spray dried, powdered complex of enhanced aluminum chlorohydrate and propylene glycol, which complex may then be dissolved in alcohol.

Two methods of making polyhydric alcohol solutions of antiperspirant salts are described in EP 295,070 and EP 404,533. In these methods a powdered antiperspirant salt, which may be an enhanced efficacy salt, is dissolved directly in a polyhydric alcohol, such as propylene glycol. In the former case, the polyhydric alcohol contains about 10 to 20% water. In the latter case, the antiperspirant salt has a water content greater than 10%.

A method of making polyhydric alcohol solutions of antiperspirant salts which are free of unbound water is described in U.S. Pat. No. 4,781,917. In that method, a powdered antiperspirant salt, which may be an enhanced efficacy salt, is dissolved in water (a 50% solution is exemplified), a polyhydric alcohol, such as propylene glycol, is added to the aqueous solution, then all of the water is removed by heating under vacuum. In U.S. Pat. No. 5,463,098, example 21 describes a method of making a propylene glycol solution of an aluminum-zirconium antiperspirant salt neutralized with zinc glycinate. An aqeous solution of aluminum chlorohydrate is refluxed in the presence of a small amount of propylene glycol, the solution is cooled to 70° C., zirconyl hydroxychloridegly is added, the solution is cooled to 40° C., then zinc glycinate followed by propylene glycol is added. This solution is then distilled under vacuum to remove water, leaving a 30% by weight solution of antiperspirant active in propylene glycol. Other examples describe spray drying the product in order to recover the powdered antiperspirant active, which is said to be soluble in liquid diols.

In WO 96/14052 there is disclosed a process of preparing a solution of an enhanced efficacy aluminum antiperspirant salt in a polyhydric alcohol by (a) providing an aqueous solution consisting essentially of about 5% to about 20% by weight of an enhanced efficacy aluminum antiperspirant salt in water, the enhanced efficacy aluminum antiperspirant salt having been prepared in situ without having been dried to a solid powder; (b) mixing the aqueous solution with a sufficient amount of a liquid polyhydric alcohol (e.g. propylene glycol) to provide a mixed solution which has an antiperspirant salt to polyhydric alcohol ratio of about 1:4 to about 1.2:1; and (c) rapidly evaporating the water from the mixed solution under vacuum to provide a liquid polyhydric alcohol solution containing about 20 to 50% enhanced efficacy aluminum antiperspirant salt and about 2 to 16% water, with the balance being said polyhydric alcohol. When an aluminum-zirconium complex is desired in the final product, the zirconium salt can be added at any stage prior to the evaporation step (c). If the water content exceeds 16%, the peak 4 to 3 ratio of the salt will deteriorate on storage.

SUMMARY OF THE INVENTION

The present invention embraces new methods of making enhanced efficacy antiperspirant salts and particularly stabilized solutions of such salts. One such method involves stabilizing an aqueous solution of an enhanced efficacy aluminum or aluminum-zirconium antiperspirant salt against rapid degradation of the HPLC peak 4 to peak 3 area ratio of said salt by adding to said aqueous antiperspirant salt solution an effective amount of a polyhydric alcohol having from 3 to 6 carbon atoms and from 3 to 6 hydroxyl groups to form a stabilized aqueous antiperspirant salt solution. A second disclosed method involves preparing an enhanced efficacy aluminum antiperspirant salt by heating an aqueous solution of an aluminum antiperspirant salt in the presence of a polyhydric alcohol having from 3 to 6 carbon atoms and from 3 to 6 hydroxyl groups at a temperature of at least 50° C. for a time sufficient to convert the salt to an enhanced salt.

A third disclosed method is an improvement in the method of making an aluminum hydroxy halide or an aluminum hydroxy nitrate by reacting aluminum with an aqueous solution of aluminum halide or aluminum nitrate (or with aqueous hydrogen halide or nitric acid), wherein the improvement comprises including a polyhydric alcohol having from 3 to 6 carbon atoms and from 3 to 6 hydroxyl groups in the reaction mixture. This method provides an aqueous solution of an aluminum antiperspirant salt of the formula $Al_2(OH)_{6-a}X_a$ wherein X is Cl, Br, I or $NO_3$ and a is about 0.3 to about 5 by reacting aluminum with an aqueous solution of $AlX_3$ or HX, wherein the amount of aluminum, the amount of $AlX_3$ or HX, and the time and temperature of reaction are selected so as to provide said antiperspirant salt of the formula $Al_2(OH)_{6-a}X_a$ at a concentration of about 5% to about 45% (USP) by weight, and wherein said aqueous solution of $AlX_3$ or HX additionally comprises a polyhydric alcohol having from 3 to 6 carbon atoms and from 3 to 6 hydroxyl groups in an amount of about 5% to about 40% by weight of the reaction mixture. Also disclosed are compositions produced by the foregoing methods. These include compositions comprising, in percent by weight (USP), about 18 to 45% of an enhanced efficacy aluminum or aluminum-zirconium antiperspirant salt, about 20 to 70% water, and about 5 to 60% of a polyhydric alcohol having from 3 to 6 carbon atoms and from 3 to 6 hydroxyl groups. The HPLC peak 4 to peak 3 area ratio of the antiperspirant salt in these compositions does not degrade as quickly or to as low a point as similar compositions without the polyhydric alcohol.

DETAILED DESCRIPTION OF THE INVENTION

Preferred aluminum salts are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X is Cl), especially ⅚ basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "ACH/ZHC" or as "AZ" herein.

The aluminum and aluminum-zirconium salts of the present invention are of the enhanced efficacy type. By "enhanced efficacy salts" is meant antiperspirant salts which, when reconstituted as 10% aqueous solutions (or if already a solution, diluted with water to about 10% salt concentration in solution), produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and more preferably at least 0.9 or higher. Most preferred are salts which exhibit an HPLC peak 4 to peak 3 area ratio of at least 3, particularly at least 5, when measured within two hours of preparation, and which retain a peak 4 to peak 3 area ratio of at least 1, preferably at least 1.5, and most preferably at least 2, when stored as an aqueous solution of at least 20% salt concentration for one month. Especially preferred are salts wherein at least 40%, more preferably at least 60%, most preferably at least 80%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH'" herein. Enhanced efficacy aluminum-zirconium chlorohydrate is referred to as "ACH'/ZHC" or as "AZ'" herein.

The polyhydric alcohol stabilized enhanced antiperspirant salts of the present invention have a distinct advantage over previously known enhanced antiperspirant salts in that they will maintain their enhanced state (i.e they will maintain an elevated peak 4 to peak 3 ratio) in aqueous solution (i.e. solutions containing more than 16% water, typically 20% to 70% water), even at relatively high salt concentrations—for example, at salt concentrations of 18% to 45% (USP) by weight.

Polyhydric alcohols which may be utilized in the present invention are those having from 3 to 6, preferably 4 to 6, carbon atoms and from 3 to 6, preferably 4 to 6, hydroxyl groups. The term "polyhydric alcohol", when used throughout this specification, will have this meaning unless otherwise indicated. Such polyhydric alcohols include glycerol, pentaerythritol, sorbitol, xylitol, dulcitol, mannitol, mesoerythritol, butanetriol, trimethylolpropane, adonitol, arabitol, threitol, inositol, scyllitol, iditol, 2,5-anhydro-D-mannitol, 1,6-anhydro-glucose, and hexanetriol. Pentaerythritol, xylitol and sorbitol are preferred, with pentaerythritol being most preferred.

Stabilization of Pre-formed Enhanced Antiperspirant Salts with Polyhydric Alcohol.

One aspect of the present invention involves the stabilization of pre-formed enhanced efficacy antiperspirant salts by the addition of a polyhydric alcohol, preferably a polyhydric alcohol having 4 to 6 carbon atoms and 4 to 6 hydroxyl groups. That is, a conventional enhanced antiperspirant salt, which would ordinarily lose peak ratio rapidly in aqueous solution, particularly at higher concentrations, may be stabilized by the addition of polyhydric alcohol to an aqueous solution of the antiperspirant salt. By "stabilized" is meant that the peak 4 to peak 3 ratio, while it may degrade somewhat, will not degrade as quickly or to as low a point as an unstabilized salt (i.e. salt solution without polyhydric alcohol present). To achieve stabilization the composition will comprise in percent by weight (USP) about 18 to 45%, preferably 20 to 42%, antiperspirant salt, about 20 to 70%, preferably 25 to 60%, water, and about 5 to 60%, preferably 10 to 40%, polyhydric alcohol. This aspect of the invention may be demonstrated by the following example.

EXAMPLE 1A

An enhanced aluminum chlorohydrate (ACH') powder, which was prepared by heating an approximately 10% aqueous solution of ACH at about 85° C. for about 16 to 20 hours then spray dried, was redissolved in water to make aqueous solutions containing the concentration of ACH' and polyhydric alcohol indicated in Table 1A below. The HPLC peak 4 to peak 3 area ratio is also given in the Table for various times after preparation.

TABLE 1A

Stability of 4/3 Ratio of Aqueous ACH'/Polyhydric Alcohol Solution From ACH' Powder

| | | | | 4/3 ratio | |
| --- | --- | --- | --- | --- | --- |
| Alcohol (%) | ACH' (%) | Water (%) | t = 0 | t = 7 days | t = 17 days (45° C.) |
| None | 20% | 80% | 1.11 | 0.25 | |
| Glycerol (40%) | 20% | 40% | | 0.35 | |
| Sorbitol (40%) | 20% | 40% | | 0.46 | |
| Xylitol (40%) | 20% | 40% | | 0.52 | |
| None | 20% | 80% | 0.7 | | 0.18 |
| Pentaerythritol (10%) | 20% | 70% | | | 0.33 |

EXAMPLE 1B

A solution of ACH' was prepared by heating a 10% ACH solution at about 80° C. for about 16 hours. Sufficient ZHC (without glycine) was added to give an Al:Zr ratio of about 3.6 and the solution was immediately freeze-dried to preserve the 4/3 ratio and prevent gellation. The Al-Zr powder was redissolved to provide aqueous solutions containing 20% ACH'/ZHC and the indicated polyhydric alcohol or, as a control, 20% ACH'/ZHC in water alone (i.e. no polyhydric alcohol). These solutions were analyzed by HPLC and the results are reported in Table 1B.

TABLE 1B

Solutions of 20% ACH'/ZHC in Water and Aqueous Polyhydric Alcohol

| | 4/3 ratio | |
| --- | --- | --- |
| Alcohol (%) | t = 0 | t = 14 days |
| None | 2.60 | gelled in 45 min. |
| Glycerol (56%) | | 0.81 |
| Sorbitol (56%) | | 2.4 |
| Xylitol (20%) | | 0.57 (t = 17 days) |

Heat Treating Antiperspirant Salt Solutions in the Presence of Polyhydric Alcohol A second aspect of the present invention involves heat treating aqueous solutions of non-enhanced antiperspirant salts, particularly ACH, in the presence of a polyhydric alcohol to form solutions of enhanced antiperspirant salts, particularly ACH'. That is, the heat treatment conversion of aqueous ACH to aqueous ACH' is performed in the conventional manner using well-known prior art techniques (see, for example GB 2,048,229 and U.S. Pat. No. 4,359,456) except that a polyhydric alcohol is added to the solution, typically in an amount of about 2% to about 40%, preferably about 5% to about 30%, more preferably about 10% to about 20%. The heat treatment is generally conducted at a temperature of at least 50° C., preferably at least 80° C., for a time sufficient to convert the aluminum salt to enhanced efficacy form (typically 2 to 20 hours). The aluminum salt concentration is generally at about 5 to 18% (USP), preferably about 8 to 15% (USP), during the heat treatment conversion, although higher concentrations, up to about 50% (i.e. about 20 to 42% USP), may be converted to enhanced form at high temperatures (e.g. at 120° to 140° C. in a closed reactor). The solution of enhanced antiperspirant salt produced will have a stabilized peak 4 to peak 3 ratio. Enhanced salts prepared in this manner will be referred to as ACH'/PA, where PA refers to the polyhydric alcohol added during the heat treatment. Thus, ACH'/P refers to ACH' made by heat treating ACH in the presence of pentaerythritol.

The inclusion of a polyhydric alcohol in the aqueous solution is especially advantageous for high temperature heat treatment—that is, heat treatment at temperatures in excess of 95° C., preferably 100° to 105° C. Such high temperature heat treatment produces exceptionally high peak 4/3 ratios (typically higher than 2, preferably higher than 3) in relatively short reaction times (typically under 15 hours, preferably about 5 to 12 hours). However, such heat treatment without polyhydric alcohol also produces a substantial amount of peak 1 aluminum species (high molecular weight), which causes the solution to become cloudy, and which may cause the solution to become very viscous or to gel at longer reaction times (e.g. at low salt concentrations), rendering it essentially unuseable. Inclusion of polyhydric alcohol in accordance with the present invention inhibits the formation of peak 1 aluminum, making the high temperature heat treatment commercially practical. ACH' solutions produced by this technique will typically have a peak 1 content of less than 0.6%, preferably less than 0.1%.

A zirconium antiperspirant salt, preferably in aqueous solution, may be added to the aqueous polyhydric alcohol solution of the enhanced efficacy aluminum antiperspirant salt prepared as described above to provide an enhanced efficacy aluminum-zirconium antiperspirant salt. Generally, the amount of zirconium salt will be an amount sufficient to provide an Al:Zr ratio of about 2 to about 10.

EXAMPLE 2A

Standard 50% (~41% USP) aluminum chlorohydrate (ACH) was diluted with water to about 10% concentration (8–10% USP) then heat treated under the conditions shown in Table 2A with and without the polyhydric alcohols indicated. The HPLC peak 4 to peak 3 area ratio was measured shortly after preparation and at a later time as indicated. For the high temperature treated material, the relative peak 1 percentage shortly after preparation is also given.

TABLE 2A

Heat Treatment of 8 or 10% ACH in the Presence of Polyhydric Alcohol

| | Heat Treatment | | 4/3 ratio | |
| --- | --- | --- | --- | --- |
| Alcohol (%) | temp/time | peak 1(%) | t = 0 | t = 17 days |
| 8% ACH | | | | |
| None | 80° C./17 h | | 1.12 | 0.57 |
| Sorbitol (5%) | " | | 1.15 | 0.65 |
| Pentaerythritol (5%) | " | | 1.16 | 0.77 |
| 10% ACH | | | | |
| None | 105° C./14 h | 0.96 | 1.52 | 0.73 |
| Xylitol(10%) | " | 0 | 2.08 | 1.43 |
| Xylitol (20%) | " | 0 | 2.31 | 1.77 |
| Pentaerythntol (10%) | " | 0 | 3.26 | 1.54 |

The addition of polyhydric alcohol to aqueous ACH solutions also facilitates conversion of high concentration ACH solutions (typically about 20% to about 42% USP) to enhanced ACH' at high temperature and pressure (typically about 120° C. to about 140° C., preferably about 130° C., closed reactor). In the presence of polyhydric alcohol this reaction proceeds to a much higher peak 4 concentration without the formation of large aluminum polymers and precipitates that normally occur under these conditions.

EXAMPLE 2B

Standard 50% (41% USP) aluminum chlorohydrate (ACH) was heated in an autoclave at 130° C. without and with 18% pentaerythritol for 18 and 15 hours respectively. The results are shown in Table 2B. The solution without pentaerythritol contained aluminum precipitates, 31.28% peak 2 aluminum and only 4.66% peak 4 aluminum. The solution with pentaerythritol contained no aluminum precipitates, trivial peak 2 aluminum and 40.24% peak 4 aluminum.

TABLE 2B

Heat Treatment of Conc. ACH in the Presence of Polyhydric Alcohol At High T And P

| ACH (%)/Alc (%) | HeatTreatment | | HPLC Peak % | | | |
|---|---|---|---|---|---|---|
| | temp/time | Precip. | 2 | 3 | 4 | 5 |
| ACH (41%) | none | — | 36.3 | 50.83 | 8.81 | 4.05 |
| ACH (41%) | 130° C./18 h | yes | 31.28 | 61.40 | 4.66 | 2.67 |
| ACH (32%)/ PE (18%) | 130° C./15 h | no | 0* | 52.79 | 40.24 | 6.97 |

*peak 2 appears as a shoulder to peak 3

Reaction of Al with AlX₃ or HX in the Presence of Polyhydric Alcohol

A third aspect of the present invention, and perhaps the most significant aspect, involves the reaction of aluminum (Al) with aluminum halide or aluminum nitrate ($AlX_3$), typically $AlCl_3$, or with hydrogen halide or nitric acid (HX), typically HCl, to form the aluminum halohydrate (hydroxyhalide) or aluminum hydroxy nitrate ($Al_2(OH)_{6-a}X_a$), typically aluminum chlorohydrate (ACH). This reaction is well-known and is the method generally utilized to prepare conventional, non-enhanced 50% (~41% USP) ACH solutions on a commercial basis. It has been suggested that enhanced aluminum chlorohydrate (ACH') can be prepared directly by this reaction if the reactants are mixed at a relatively dilute concentration so that the final concentration of ACH' in the solution is below 20%, preferably about 10%. In this regard see, for example, U.S. Pat. No. 4,859,446, U.S. Pat. No. 4,944,933, and U.S. Pat. No. 5,356,609. This direct synthesis of ACH' has little or no advantage over the known heat treatment of dilute ACH to form ACH' since dilute solutions are still required, making it necessary to remove large quantities of water to obtain the desired product in powder form, the only form in which the product is stable. In addition, this direct synthesis suffers from the significant disadvantage in that a substantial amount of $Al^b$ is produced, typically about 20 to 60% of the total aluminum. This is in contrast to the 2 to 5% $Al^b$ produced in the conventional heat treatment of ACH to form ACH'. This $Al^b$, which does not provide enhanced efficacy, also appears in peak 4 along with the enhanced $Al^c$.

In accordance with the present invention, it was discovered that if the reaction of aluminum with aluminum halide (or hydrogen halide) or with aluminum nitrate (or nitric acid) is performed in the presence of polyhydric alcohol, enhanced aluminum halohydrate or aluminum hydroxy nitrate is preferentially formed even at relatively high concentrations (i.e. at concentrations greater than 20%). Moreover, such concentrated solutions have an initial HPLC peak 4 to 3 area ratio substantially higher than conventionally prepared enhanced salts (typically 0.9 or higher, preferably 3.0 or higher, more preferably 5.0 or higher) and the peak ratio is stabilized in an enhanced state (i.e. the peak ratio remains greater than 0.5, preferably greater than 1) for at least one month. In addition, the amount of $Al^b$ in the salt (as measured by the ferron test) is less than 10% of the total aluminum, preferably less than 5%.

The above-described reaction may be carried out within the following parameters. The amount of aluminum and aluminum halide (or aluminum nitrate or hydrogen halide or nitric acid) added will be an approximately stoichiometric amount (although a slight excess of aluminum may be desired) so as to provide about a 5% to about a 45% (USP) solution, preferably about a 20% to 42% (USP) solution, of the enhanced aluminum halohydrate (or aluminum hydroxy nitrate) desired. Concentrations above 20% are preferred for economic efficiency. The amount of polyhydric alcohol may range from about 5% to about 40%, preferably about 10% to about 35%, by weight of the final solution. Obviously, too little polyhydric alcohol will not achieve the desired benefit and too much may be economically impractical or may interfere with the reaction or the ultimate use of the product. The temperature of the reaction may be from about 50° C. to about 120° C., preferably about 800 to 105° C., and the reaction time may vary, depending on the reaction temperature, from about 1 to 100 hours, preferably about 3 to 12 hours, most preferably about 4 to 6 hours. Generally, the reaction will be carried out until the desired aluminum to halide (or nitrate) ratio is achieved (broadly 0.8 to 2.5, and typically 1.9 to 2.1 for ⅚ ACH'). The enhanced ACH prepared in this manner will be referred to as polyhydric alcohol included ACH' (hereinafter "PA-ACH'"). Thus, enhanced ACH prepared by synthesis in the presence of pentaerythritol is referred to as pentaerythritol-included ACH' or P-ACH'.

EXAMPLE 3

Solutions of ⅚ ACH' were prepared by reacting, at about 100° C. in a flask fitted with a condenser, an appropriate amount of Al and $AlCl_3$ in an aqueous solution containing a polyhydric alcohol to provide the desired concentration of ACH'. The final concentration of the ACH' in solution and the identity and concentration (as added) of the polyhydric alcohol are indicated in Table 3. After cooling and filtering the solution, the HPLC peak 4 to peak 3 area ratio was measured. As an example of the process, the second solution given in the Table was made by reacting at 105° C. for about 6 hours 5.79 g Al with 10.66 g $AlCl_3 \cdot 6H_2O$ in 39.93 g of 70% sorbitol and 36.78 g water to provide an aqueous 25% ACH'/30% sorbitol solution. Similarly, the next to last solution in the Table was made by reacting at 105° C. for about 6 hours 5.7 g Al with 10.66 g $AlCl_3 \cdot 6H_2O$ in 27.95 g of pentaerythritol and 48 g water. The other solutions shown in the Table were made in a similar manner by adjusting the reactants accordingly. Since some of the polyhydric alcohols, such as pentaerythritol, are only partially soluble in water at room temperature, filtering also removes precipitated polyhydric alcohol. Thus, the final solution obtained may contain less polyhydric alcohol than was added initially. In the case of pentaerythritol, the final ACH' solution contains about 6 to 15% pentaerythritol. The percentage of polyhydric alcohol indicated in Table 3 represents the amount initially added to the reaction mixture.

TABLE 3

Preparation of ACH' by Reaction of Al + AlCl$_3$ in Aqueous Polyhydric Alcohol

| | | 4/3 ratio | | |
|---|---|---|---|---|
| Alcohol (%) | ACH' (%) | t = 0 | t = 3 days | t = 8 days |
| None | 25% | 0.28 | 0.20 | |
| Sorbitol (30%) | 25% | 2.76 | 2.41 | |
| Sorbitol (30%) | 30% | 2.12 | 1.90 | |
| Sorbitol (30%) | 35% | 1.67 | 1.46 | |
| d-Mannitol (30%) | 25% | 0.74 | | |
| Dulcitol (30%) | 25% | 0.92 | | |
| Xylitol (30%) | 25% | 3.27 | | |
| Pentaerythritol (30%)* | 25% | 15.17 | | 8.24 |
| Pentaerythritol (30%)* | 37% | 10.52 | | 8.20 |

*30% during reaction; <15% after cooling and filtering.

EXAMPLE 4

A 250 mL round-bottom flask was loaded with 10.5 g AlCl$_3$.6H$_2$O, 33.0 g pentaerythritol ("PE") and 40.0 g distilled water. It was fitted with a water condenser and heated in a heating mantle. After the mixed reactants were heated to reflux at 104° to 105° C., 5.7 grams of aluminum atomized powder were added slowly. The reaction proceeded under magnetic stirring for 2 hours after the addition of aluminum powder. The product was cooled to room temperature, at which most of the added pentaerythritol had crystallized out and was removed by filtration with Whatman #44 filter paper to give a clear solution of pentaerythritol-included enhanced ACH (hereinafter "P-ACH'"). This experiment was repeated with reaction times of 4 and 6 hours. This experiment was also repeated without the pentaerythritol, which was replaced by water, to replicate the conventional production of non-enhanced 50% ACH (41% USP or 12.5% Al). The results of these experiments along with HPLC relative peak area percentages are reported in Table 4. From this experiment it will be seen that a reaction time of 4 to 6 hours is sufficient to complete the reaction. Moreover, the reaction in the presence of pentaerythritol produces an enhanced ACH with about 90% of the Al in peak 4. In contrast, 50% (41% USP) ACH, which is prepared by the same reaction, but without pentaerythritol, has only about 9% of the Al in peak 4, the bulk of it being contained in peaks 2 and 3.

TABLE 4

Reaction of 6.4% Al/6.5% AlCl$_3$/37% PE/50.1% H$_2$O at 105° C. for Various Times

| | HPLC Peak % | | | | 4/3 | | | |
|---|---|---|---|---|---|---|---|---|
| Time | 2 | 3 | 4 | 5 | ratio | % Al | % Cl | Al/Cl |
| 2 hr | 0 | 8.95 | 72.39 | 18.66 | 8.09 | 10.76 | 10.09 | 1.40 |
| 4 hr | 0 | 6.87 | 90.52 | 2.62 | 13.18 | 11.05 | 7.31 | 1.99 |
| 6 hr | 0 | 6.17 | 93.83 | 0 | 15.21 | 11.07 | 7.42 | 1.96 |
| 6 hr (no PE) | 21.6 | 67.2 | 8.83 | 2.37 | 0.13 | 12.3 | 8.12 | 1.99 |

EXAMPLE 5

The experiment described in Example 4 was repeated at the 6 hour reaction time except that in addition to 5.7 g Al, 4.0 g and 2.8 g of Al were added to the reaction mixture. The results are presented in Table 5. It will be seen that an enhanced P-ACH' is produced corresponding to 5/6, 3/4 and 2/3 aluminum chlorohydrate.

TABLE 5

Production of 5/6, 3/4 and 2/3 P-ACH' by Varying Amount of Al in Al/AlCl$_3$/PE Reaction

| | HPLC Peak % | | | 4/3 | | | | % |
|---|---|---|---|---|---|---|---|---|
| Al (g) | 3 | 4 | 5 | ratio | % Al | % Cl | Al/Cl | ACH (type) |
| 5.7 g | 6.17 | 93.83 | 0 | 15.21 | 11.07 | 7.42 | 1.96 | 36% (5/6) |
| 4.0 g | 8.73 | 73.27 | 17.99 | 8.36 | 8.16 | 7.48 | 1.43 | 28% (3/4) |
| 2.8 g | 7.21 | 58.82 | 33.97 | 8.16 | 7.23 | 8.46 | 1.12 | 23% (2/3) |

EXAMPLE 6

The experiment described in Example 4 was repeated at the 6 hour reaction time except that in addition to 33.0 g pentaerythritol, 25.0 g and 15.0 g of pentaerythritol were added to the reaction mixture. The results are presented in Table 6. It will be seen that as the amount of pentaerythritol increases, the amount of Al in peak 4 increases as peaks 2 and 3 decrease.

TABLE 6

Production of 5/6 P-ACH' by Varying Amount of PE in Al/AlCl$_3$/PE Reaction

| | HPLC Peak % | | | | 4/3 | | | |
|---|---|---|---|---|---|---|---|---|
| PE (g) | 2 | 3 | 4 | 5 | ratio | % Al | % Cl | Al/Cl |
| 33.0 g | 0 | 6.17 | 93.83 | 0 | 15.21 | 11.07 | 7.42 | 1.96 |
| 25.0 g | 0 | 11.87 | 88.13 | 0 | 7.42 | 10.84 | 7.37 | 1.93 |
| 15.0 g | 11.58 | 21.53 | 66.90 | 0 | 3.11 | 11.18 | 7.44 | 1.97 |

Preparation of Al-Zr/polyhydric Alcohol Solutions and Inhibition of Gellation without Glycine.

It is well-known in the antiperspirant art that the addition of zirconium salts, typically zirconyl hydroxychloride ("ZHC"), to aqueous aluminum salts, typically aluminum chlorohydrate, causes the solution to gel, rendering it unuseable. This problem has been solved by the inclusion of certain amino acids, typically glycine, in the solution, usually in the aqueous zirconyl solution which is added to the aqueous aluminum chlorohydrate solution. Consequently, all commercially available Al-Zr antiperspirant salts, including enhanced salts, contain glycine and are referred to as Al-Zr-Gly (or sometimes ZAG).

In accordance with the present invention, enhanced Al-Zr salts may be prepared by adding to an aqueous solution of the polyhydric alcohol included ACH', made as described previously (e.g. P-ACH' as described in Ex. 4), an amount of zirconium salt (e.g. zirconyl hydroxychloride) sufficient to provide the desired Al:Zr ratio (typically between 2 and 10). However, unlike the conventional method, the present method does not require glycine since the polyhydric alcohol inhibits gellation of the solution upon addition of the zirconium. In fact, quite surprisingly, the presence of glycine in significant quantities (e.g. Gly:Zr≧1) causes a solution of P-ACH'/ZHC (referred to hereinafter as "P-AZ") to gel. Gellation of P-AZ-gly occurs faster as concentration of P-AZ increases, as temperature increases, as glycine content increases, and as Al:Zr ratio decreases.

EXAMPLE 7

A P-ACH' solution of approximately 36% ACH' concentration was prepared in accordance with Example 4 (about 6 hours reaction time). To separate and approximately equal portions of this solution was added a sufficient quantity of aqueous zirconyl hydroxychloride (ZHC) or zirconyl hydroxychloride-glycine (ZHC-gly; Zr:Gly=1) to provide an Al:Zr ratio of about 3.6. The ZHC aqueous solution was about 35% ZHC concentration and was heat treated for about 3 hours at 95° C. prior to addition of glycine (when present) and prior to being added to the P-ACH' solution. The resultant P-AZ and P-AZ-gly solutions, which contained about 35% and 33% Al-Zr salt respectively, were filtered and analyzed via HPLC. The results are given in Table 7. The P-AZ-gly solution gelled in about 3–5 days at room temperature, while the P-AZ solution (without glycine) remained a clear solution for one month. For comparison, solutions of enhanced Al-Zr and Al-Zr-gly were prepared in the conventional manner by heating a 10% ACH solution for about 17 hours at 85° C., then adding ZHC or ZHC-gly (Gly:Zr=1) solution as above to provide solutions with an Al:Zr ratio of about 3.6. Each solution was immediately spray dried to a powder, then the powder was redissolved in water at 30% concentration. These solutions were analyzed via HPLC and the results are reported in Table 7

TABLE 7

Production of P-AZ and P-AZ-gly vs. enhanced Al—Zr and Al—Zr-gly

| Solution (%) | 4/3 ratio | | |
|---|---|---|---|
|  | t = 0 | t = 3–5 days | t = one month |
| P-AZ (35%) | 11 |  | 2.5 (sol'n) |
| P-AZ-gly (33%) | 11 | gel | gel |
| Al—Zr (30%) | gel | gel | gel |
| Al—Zr-gly (30%) | 1.2 |  | 0.1 (sol'n) |

Gellation of Polyhydric Alcohol Included ACH'

It has been found that solutions of polyhydric alcohol included ACH' (PA-ACH'), particularly pentaerythritol included ACH' (P-ACH'), will gel upon addition of an amino acid such as glycine. This gellation is independent of the presence of zirconium, unlike conventional antiperspirant salts, although the gellation will also occur, as shown in Example 7, with zirconium present (i.e. P-AZ). In fact, the gellation of P-AZ is probably due to the interaction of the P-ACH' with glycine. In contrast, gellation does not occur with ACH'/P, i.e. ACH' made by heat treating ACH in the presence of pentaerythritol. The rapidity of gellation and the hardness of the gel will increase with increasing salt concentration and glycine content.

EXAMPLE 8

To separate portions of a P-ACH' solution of approximately 36% ACH' concentration prepared in accordance with Example 4 (about 6 hours reaction time) was added sufficient glycine to provide two solutions with an Al:Gly ratio of 1:1 and 1:2 respectively. These two solutions gelled in about four days and two days respectively. The gel hardness changes from a soft gel to a firm stick with time. For comparison, ACH' was prepared by reacting 5.7 g of Al with 10.5 g $AlCl_3 \cdot 6H_2O$ in 45 g water at about 100° C. for about 6 hours and filtering the resultant product. To this solution was added sufficient glycine to provide an Al:Gly ratio of about 1:1. This solution did not form a gel in one month.

Throughout the specification reference to HPLC analysis means that chromatograms were obtained as follows: Salt solutions are evaluated for aluminum polymer distribution by HPLC at a concentration of about 10% Al or Al-Zr salt. If the solution to be analyzed is at a higher salt concentration, it is diluted with sufficient water to bring the salt concentration to about 10%. A 1.0 $\mu$L sample is pumped through a 4.6 mm×50 cm column packed with Nucleosil 100-5 (Keystone Scientific Inc.) using a 0.01M aqueous nitric acid solution as the eluent. The flow rate of the mobile phase was controlled at 0.5 mL/min with a Waters 100 unit. HPLC profiles were recorded and processed with a computerized system that included the Millennium 2010 Chromatography Manager software from the Millipore/Waters Corp. A Waters 410 differential refractometer was used as the refractive index detector. The HPLC profiles are read from left to right (higher to lower molecular weight). Following this technique, peaks 3 and 4 appear at retention times of Kd=0.32–0.38 and Kd=0.49–0.53 respectively. Naturally, of course, other HPLC techniques which use different column materials, eluents and flow rates can be used provided that they sufficiently resolve peaks 3 and 4 with an acceptable degree of precision (i.e. the technique must be capable of resolving the Al into five distinct peaks). Obviously, such other techniques may place peaks 3 and 4 at different retention times from those given above.

It should be noted that reference throughout this application to weight percent of antiperspirant salt is intended to be calculated as anhydrous weight percent in accordance with the new U.S.P. method. This calculation excludes any bound water and glycine. For aluminum chlorohydrate and aluminum-zirconium chlorohydrate, the calculation is as follows:

%ACH=%Al[26.98x+17.01(3x-1)+35.45]/26.98x where x=Al/Cl ratio;

%Al-Zr=%Al{26.98y+92.97+17.01[3y+4-(y+1)/z]+35.45(y+1)/z}/26.98y where y=Al/Zr ratio and z=metal/Cl ratio.

For reference purposes, calculation of antiperspirant salt weight percent in accordance with the U.S.P. method compares to the previously used standard industry method as follows:

| SALT | STANDARD METHOD | USP METHOD |
|---|---|---|
| ACH (50% aqueous) | 50% | 40.8% |
| Al—Zr-Gly (50% aqueous) | 50% | 38.5% |
| P-ACH' (Ex. 4, 6 hr) | — | 36% |

What is claimed is:

1. A stabilized aqueous antiperspirant composition comprising, in percent by weight (USP), about 20 to 42% of an enhanced efficacy aluminum or aluminum-zirconium antiperspirant salt having an HPLC peak 4 to peak 3 area ratio of at least 0.5 with at least 70% of the aluminum contained in said peaks 3 and 4, about 25 to 60% water, and about 10 to 40% of a polyhydric alcohol having from 3 to 6 carbon atoms and from 3 to 6 hydroxyl groups.

2. The composition of claim 1 wherein said polyhydric alcohol has from 4 to 6 carbon atoms and from 4 to 6 hydroxyl groups.

3. The composition of claim 2 wherein said enhanced efficacy antiperspirant salt is enhanced efficacy aluminum chlorohydrate or enhanced efficacy aluminum-zirconium chlorohydrate.

4. The composition of claim 3 wherein said polyhydric alcohol is pentaerythritol.

5. A method of stabilizing an aqueous solution of an enhanced efficacy aluminum or aluminum-zirconium antiperspirant salt against rapid degradation of the HPLC peak 4 to peak 3 area ratio of said salt, wherein said salt has an HPLC peak 4 to peak 3 area ratio of at least 0.5 with at least 70% of the aluminum contained in said peaks 3 and 4, said method comprising adding to said aqueous enhanced efficacy antiperspirant salt solution an effective amount of a polyhydric alcohol having from 3 to 6 carbon atoms and from 3 to 6 hydroxyl groups to form a stabilized aqueous enhanced efficacy antiperspirant salt solution comprising about 20 to 42% of said antiperspirant salt, about 25 to 60% water, and about 10 to 40% of said polyhydric alcohol.

6. The method of claim 5 wherein said polyhydric alcohol has from 4 to 6 carbon atoms and from 4 to 6 hydroxyl groups.

7. The method of claim 6 wherein said enhanced efficacy antiperspirant salt is enhanced efficacy aluminum chlorohydrate or enhanced efficacy aluminum-zirconium chlorohydrate.

8. The method of claim 7 wherein said polyhydric alcohol is pentaerythritol.

9. A method of preparing a stabilized aqueous enhanced efficacy aluminum antiperspirant salt solution which comprises heating an aqueous solution of an aluminum antiperspirant salt in the presence of a polyhydric alcohol having from 4 to 6 carbon atoms and from 4 to 6 hydroxyl groups at a temperature of at least 50° C. for a time sufficient to convert the aluminum antiperspirant salt to an enhanced efficacy aluminum antiperspirant salt having an HPLC peak 4 to peak 3 area ratio of at least 0.5 with at least 70% of the aluminum contained in said peaks 3 and 4.

10. The method of claim 9 wherein said aqueous solution comprises, in percent by weight, about 5 to about 42% (USP) aluminum antiperspirant salt and about 2 to about 40% polyhydric alcohol.

11. The method of claim 10 wherein said heating is conducted at a temperature of at least 80° C.

12. The method of claim 10 wherein said heating is conducted at a temperature of about 100° C. to about 105° C.

13. The method of claim 10 wherein said heating is conducted at a temperature of about 120° C. to about 140° C. in a closed reactor.

14. The method of claim 11 or 12 wherein said aqueous solution comprises about 5% to about 18% (USP) aluminum antiperspirant salt.

15. The method of claim 13 wherein said aqueous solution comprises about 20% to about 42% (USP) aluminum antiperspirant salt.

16. The method of claim 14 wherein said aluminum antiperspirant salt is an aluminum chlorohydrate.

17. The method of claim 15 wherein said aluminum antiperspirant salt is an aluminum chlorohydrate.

18. The method of claim 10 or 17 wherein said aqueous solution comprises about 5 to about 30% polyhydric alcohol.

19. The method of claim 18 wherein said polyhydric alcohol is pentaerythritol.

20. The method of claim 14 wherein said aqueous solution comprises about 5 to about 30% polyhydric alcohol.

21. The method of claim 20 wherein said polyhydric alcohol has from 4 to 6 carbon atoms and from 4 to 6 hydroxyl groups.

22. The method of claim 20 wherein said polyhydric alcohol is pentaerythritol.

23. The method of claim 13 wherein said enhanced efficacy aluminum antiperspirant salt has an HPLC peak 4 to peak 3 area ratio of at least 0.7 and wherein at least 70% of the aluminum is contained in said peaks 3 and 4.

24. The method of claim 13 wherein said enhanced efficacy aluminum antiperspirant salt has an HPLC peak 4 to peak 3 area ratio of at least 0.9 and wherein at least 80% of the aluminum is contained in said peaks 3 and 4.

25. The method of claim 13 which further comprises adding to said enhanced efficacy aluminum antiperspirant salt solution an aqueous solution of a zirconium antiperspirant salt in an amount sufficient to provide an Al:Zr ratio of about 2 to about 10.

26. A stabilized aqueous antiperspirant composition comprising, in percent by weight (USP), about 18 to 45% of an enhanced efficacy aluminum or aluminum-zirconium antiperspirant salt having an HPLC peak 4 to peak 3 area ratio of at least 0.5 with at least 70% of the aluminum contained in said peaks 3 and 4, about 20 to 70% water, and about 5 to 60% of a polyhydric alcohol having from 4 to 6 carbon atoms and from 4 to 6 hydroxyl groups.

27. A method of stabilizing an aqueous solution of an enhanced efficacy aluminum or aluminum-zirconium antiperspirant salt against rapid degradation of the HPLC peak 4 to peak 3 area ratio of said salt, wherein said salt has an HPLC peak 4 to peak 3 area ratio of at least 0.5 with at least 70% of the aluminum contained in said peaks 3 and 4, said method comprising adding to said aqueous enhanced efficacy antiperspirant salt solution an effective amount of a polyhydric alcohol having from 4 to 6 carbon atoms and from 4 to 6 hydroxyl groups to form a stabilized aqueous enhanced efficacy antiperspirant salt solution comprising about 18 to 45% of said antiperspirant salt, about 25 to 70% water, and about 5 to 60% of said polyhydric alcohol.

* * * * *